(12) United States Patent
Kagabu et al.

(10) Patent No.: US 6,875,778 B2
(45) Date of Patent: Apr. 5, 2005

(54) ALKYLENE-TETHERED BIS-NITROIMINOIMIDAZOLIDINES, PROCESS FOR PREPARING THE SAME, AND INSECTICIDES CONTAINING THE SAME

(75) Inventors: Shinzo Kagabu, Gifu (JP); Keiichiro Nishimura, Sakai (JP)

(73) Assignee: Gifu University

( * ) Notice: Subject to any disclaimer, the term of this patent is extended or adjusted under 35 U.S.C. 154(b) by 23 days.

(21) Appl. No.: 10/379,641

(22) Filed: Mar. 5, 2003

(65) Prior Publication Data

US 2003/0220305 A1 Nov. 27, 2003

(30) Foreign Application Priority Data

Mar. 26, 2002 (JP) ........................................ 2002-086410

(51) Int. Cl.$^7$ ...................... A01N 43/40; C07D 401/12; C07D 401/10; C07D 401/06
(52) U.S. Cl. ........................ 514/333; 514/341; 546/256; 546/272.7
(58) Field of Search ................................. 514/333, 341; 546/256, 272.7

(56) References Cited

U.S. PATENT DOCUMENTS 4,880,933 A * 11/1989 Shiokawa et al. .......... 544/332

FOREIGN PATENT DOCUMENTS

EP        0 277 317 A        8/1988

OTHER PUBLICATIONS

Kagabu et al. , "Synthesis of alkylene–tethered bis–imidaclopyrid, etc.," CA 138:304209 (2002).*
Kagabu, Shinzo et al., "Synthesis of alkylene–tthere bis–imidacloprid derivatives as highly insecticidal and nerve–exciting agents with potent affinity of '3H' imidacloprid–binding sites on nocotinic acetylcholine receptor", Nippon Noyaku Gakkaishi, 2002, 27(3), pp249–256.

* cited by examiner

Primary Examiner—Patricia L. Morris
(74) Attorney, Agent, or Firm—Robert D. Buyan; Stout, Uxa, Buyan & Mullins, LLP

(57) ABSTRACT

The present invention provides a novel alkylene-tethered bis-nitroiminoimidazolidine compound having superior insecticidal activity. The nitroimino imidazolidine compound is a bis-[1-(pyridylmethyl)-2-nitroiminoimidazolidinyl)alkylene compound represented by chemical formula 1.

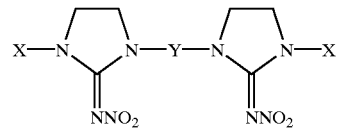

(1)

In formula 1, Y represents an alkylene group having 3 to 10 carbon atoms, —$CH_2CH=CHCH_2$—, —$CH_2C\equiv CCH_2$—, —$(CH_2)_3O(CH_2)_3$—, —$(CH_2)_3S(CH_2)_3$—,

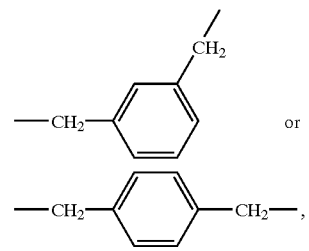

X represents a pyridylmethyl group composed of

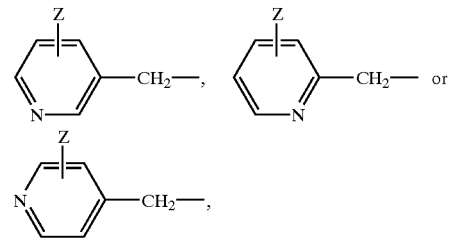

and Z represents a halogen atom, $CH_3$, or H.

9 Claims, No Drawings

ALKYLENE-TETHERED BIS-NITROIMINOIMIDAZOLIDINES, PROCESS FOR PREPARING THE SAME, AND INSECTICIDES CONTAINING THE SAME

BACKGROUND OF THE INVENTION

The present invention relates to a novel compound having insecticidal activity, and more particularly, to an alkylene-tethered bis-nitroiminoimidazolidine compound having insecticidal activity, a process for preparing the same, and an insecticide.

Examples of compounds having insecticidal activity include nitromethylene derivatives such as 1-(3-pyridylmethyl)-2-(nitromethylene)imidazolidine and their salts. These nitromethylene compounds have insecticidal activity against harmful insects, mites, and nematodes. This insecticidal activity is expressed corresponding to the structure of the pyridylalkyl group within 1-(3-pyridylmethyl)-2-(nitromethylene)imidazolidines.

However, since the above nitromethylene compounds are easily decomposed by light, the use of the compounds was limited.

SUMMARY OF THE INVENTION

The object of the present invention is to provide a compound having potent insecticidal activity, a process for preparing the same, and an insecticide containing the compound.

To achieve the above object, the present invention provides a compound represented by chemical formula 1.

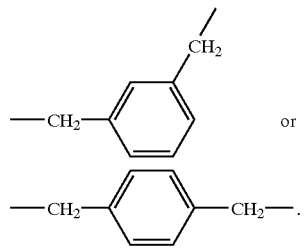

(1)

In formula 1, Y represents an alkylene group having 3 to 10 carbon atoms, $-CH_2CH=CHCH_2-$, $-CH_2C\equiv CCH_2-$, $-(CH_2)_3O(CH_2)_3-$, $-(CH_2)_3S(CH_2)_3-$,

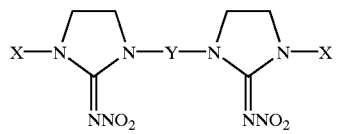

or

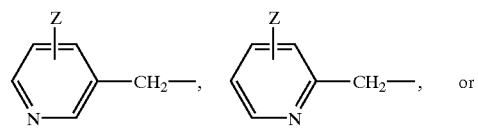

X represents a pyridylmethyl group composed of

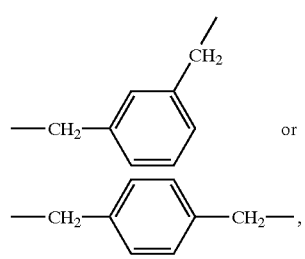

or

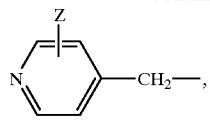

and Z represents a halogen atom, $CH_3$ or H.

Another aspect of the present invention provides a compound represented by chemical formula 2.

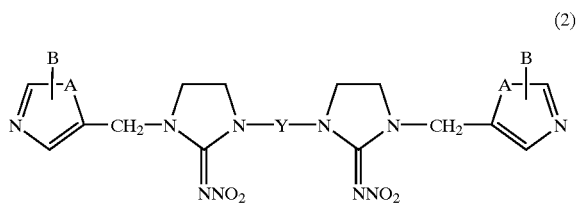

(2)

In formula 2, Y represents an alkylene group having 3 to 10 carbon atoms, $-CH_2CH=CHCH_2-$, $-CH_2C\equiv CCH_2-$, $-(CH_2)_3O(CH_2)_3-$, $-(CH_2)_3S(CH_2)_3-$,

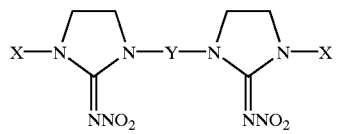

or

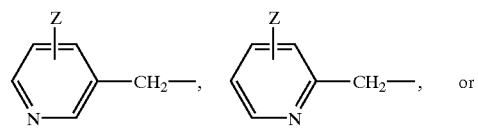

A represents $-S-$, $-O-$ or $-NH-$, and B represents a halogen atom, $CH_3$, or H.

Other aspects and advantages of the present invention will become apparent from the following description.

DETAILED DESCRIPTION OF PREFERRED EMBODIMENTS

The following provides an explanation of one embodiment of the invention.

The present invention discloses a bis[1-(pyridylmethyl)-2-nitroiminoimidazolidinyl]alkylene compound (hereinafter referred to nitroimino-imidazolidine compound A1). The nitroimino-imidazolidine compound A1 is a novel compound having the structure represented by chemical formula 1.

[Nitroinimo-imidazolidine Compound A1]

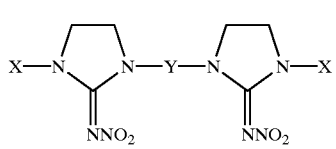

(1)

In formula 1, Y represents an alkylene group having 3 to 10 carbon atoms, $-CH_2CH=CHCH_2-$, $-CH_2C\equiv CCH_2-$, $-(CH_2)_3O(CH_2)_3-$, $-(CH_2)_3S(CH_2)_3-$,

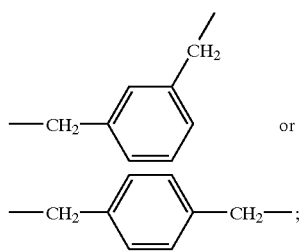

X represents a pyridylmethyl group composed of

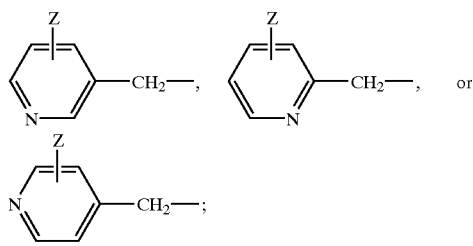

and Z represents a halogen atom, $CH_3$, or H.

The nitroimino-imidazolidine compound A1, which has bis-nitroiminoimidazolidine group and a tethering segment Y, has insecticidal activity against agricultural and sanitary harmful insects. The nitroimino-imidazolidine compound A1 has biological activity including analgesic effects and nerve activating effects. The nitroimino-imidazolidine compound A1 is able to eradicate agricultural and sanitary harmful insects without causing chemical damage or other detrimental effects on cultivated plants. Examples of harmful insects that are eradicated include insects of the Plataria, Orthoptera, Isoptera, Coleoptera, Lepidoptera, and Hemiptera orders. Common cockroaches (*periplaneta*) and waterbugs (*blattella*) are included in harmful insects of the Plataria order. Locusts and grasshoppers are included in harmful insects of the Orthoptera order. Termites are included in harmful insects of the Isoptera order. Adzuki weevils, grain weevils, cadelles, rice root beetles, mud beetles, rice weevils, cucumber beetles, and gold beetles are included in harmful insects of the Coleoptera order. Green caterpillars, gypsy moths, and flour moths are included in harmful insects of the Lepidoptera order. Aphids, leafhoppers, stinkbugs, and rice insects are included in harmful insects of the Hemiptera order.

Since the nitroimino-imidazolidine compound A1 acts on nicotinic acetylcholine receptors to activate nerves, it can be used as a therapeutic drug for neural diseases, Alzheimer's disease, Parkinson's disease and so forth.

The following provides an explanation of a preparation process of the nitroimino-imidazolidine compound A1.

Compound A1 is obtained by reacting 1-(pyridylmethyl)-2-nitroiminoimidazolidine represented by chemical formula 3 with a compound represented by chemical formula 4 in the presence of a base and in a solvent.

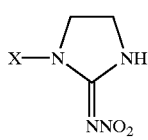

(3)

In formula 3, X represents a pyridylmethyl group composed of

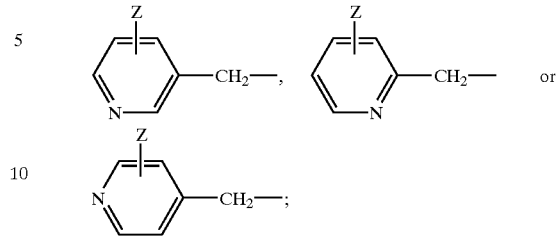

and, Z represents a halogen atom, $CH_3$, or H.

D—Y—D (4)

In formula 4, Y represents an alkylene group having 3 to 10 carbon atoms, $-CH_2CH=CHCH_2-$, $-CH_2C\equiv CCH_2-$, $-(CH_2)_3O(CH_2)_3-$, $-(CH_2)_3S(CH_2)_3-$,

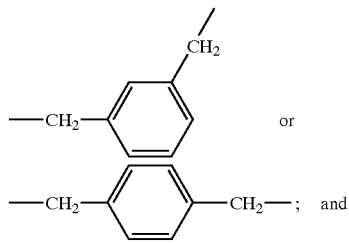

and

D represents Cl, Br, I, or

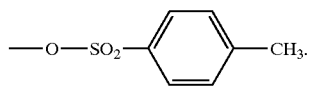

Stoichiometrically, 2 moles of a compound of chemical formula 3 and 1 mole of a compound of chemical formula 4 react to form 1 mole of nitroimino-imidazolidine compound A1 and 2 moles of by-product (HD).

The amount of a compound of chemical formula 4 to be used is preferably within the range of 0.5 to 1.2 moles relative to 1 mole of 1-(pyridylmethyl)-2-nitroiminoimidazolidine of chemical formula 3. In this case, nitroimino-imidazolidine compound A1 is normally obtained at a yield of 70% or more. In the case where the amount of a compound of chemical formula 4 to be used is less than 0.5 moles relative to 1 mole of a compound of chemical formula 3, the yield of nitroimino-imidazolidine compound A1 decreases, disadvantageously. On the other hand, in the case where this molar ratio exceeds 1.2 moles, the proportion of a compound of chemical formula 4 that does not contribute to the reaction increases, thereby making this undesirable.

Examples of bases that are used include sodium hydride (NaH), potassium carbonate ($K_2CO_3$), sodium carbonate ($Na_2CO_3$), sodium hydroxide (NaOH), potassium hydroxide (KOH), and triethylamine [$(C_2H_5)_3N$]. The amount of the base used is preferably 0.5 to 2.0-fold moles relative to the 1-(pyridylmethyl)-2-nitroiminoimidazolidine of chemical formula 3. If the amount used is less than 0.5-fold moles, the action of the base is unable to be adequately demonstrated, while even if the amount used exceeds 2.0-fold moles, yield will no longer be improved any further.

Examples of solvents that can be used include dimethylformamide (DMF), acetonitrile, dimethyl sulfoxide (DMSO), tetrahydrofuran (THF), toluene, acetone, water and alcohols such as ethanol. The preferable reaction temperature is 0 to 200° C. The reaction rate becomes slow when the reaction temperature is lower than 0° C., and the reaction proceeds too rapidly when the temperature is above 200° C., which is undesirable due to the increased susceptibility to side reactions. The reaction is typically carried out under the atmospheric pressure. The reaction time is from about 30 minutes to 24 hours.

The present invention further discloses a bis[1-(azolylmethyl)-2-nitroiminoimidazolidinyl]alkylene compound (hereinafter abbreviated as nitroimino-imidazolidine compound A2). The nitroimino-imidazolidine compound A2 is a novel compound having the structure represented by chemical formula 2. In the nitroimino-imidazolidine compound A2, the pyridylmethyl group (X) of nitroimino-imidazolidine compound A1 is substituted with an azolylmethyl group. Other structural characteristics are the same.

[Nitroinimo-imidazolidine Compound A2]

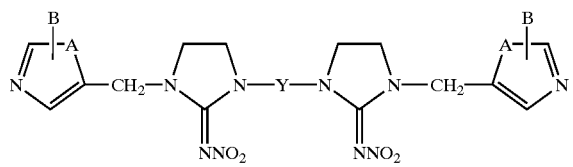

(2)

In formula 2, Y represents an alkylene group having 3 to 10 carbon atoms, $-CH_2CH=CHCH_2-$, $-CH_2C\equiv CCH_2-$, $-(CH_2)_3O(CH_2)_3-$, $-(CH_2)_3S(CH_2)_3-$,

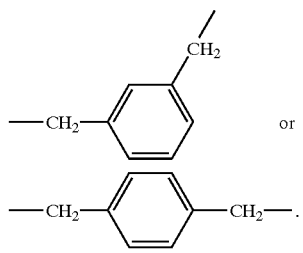

or

A represents $-S-$, $-O-$ or $-NH-$, and B represents a halogen atom, $CH_3$, or H.

The nitroimino-imidazolidine compound A2 has action that is similar to that of nitroimino-imidazolidine compound A1.

The following provides an explanation of a preparation process of the nitroimino-imidazolidine compound A2.

The nitroimino-imidazolidine compound A2 is prepared by reacting a 1-(azolylmethyl)-2-nitroiminoimidazolidine compound represented by chemical formula 5 with a dihalogen compound of chemical formula 6 in the presence of a base and in a solvent.

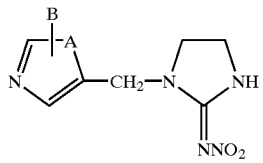

(5)

In formula 5, A represents $-S-$, $-O-$, or $-NH-$; and B represents a halogen atom, $CH_3$, or H.

$$E-(CH_2)_6-E \quad (6)$$

In formula 6, E represents a halogen atom.

The reaction conditions, namely the molar ratio of reaction raw materials, base and its amount used, solvent, reaction temperature, reaction pressure, and reaction time, are the same as those of nitroimino-imidazolidine compound A1.

The following provides an explanation of the application of nitroimino-imidazolidine compounds A1 and A2.

Since the nitroimino-imidazolidine compounds A1 and A2 have insecticidal activity on agricultural and sanitary harmful insects, analgesic action and action that activates nerves, nitroimino-imidazolidine compounds A1 and A2 can be used as the active ingredients of insecticides for agricultural and sanitary harmful insects, analgesics, and neural activators. Examples of the forms of insecticides include water-dispersible powders, emulsions, oils, sprays, powders, granules, tablets, and capsules. Examples of the solvents include methanol, ethanol, acetone, dimethyl sulfoxide (DMSO), and dimethylformamide (DMF), in addition to water. The amount of active ingredient contained is set to about 0.1 to 200 ppm.

Insecticides containing the nitroimino-imidazolidine compounds A1 and A2 may be blended as necessary with additives including diluents such as water and organic solvents, surfactants, stabilizers, binders, aerosol propellants, and synergists. Moreover, they may also be blended as necessary with other agricultural chemicals, such as insecticides, germicides, miticides, herbicides, and attractants.

The following advantages are obtained according to the present invention.

The nitroimino-imidazolidine compound A1 has a specific structure that contains a pyridylmethyl group and nitroimino group. The nitroimino-imidazolidine compound A2 has a specific structure that contains an azolylmethyl group and nitroimino group. Consequently, the nitroimino-imidazolidine compounds A1 and A2 have comparatively high biological activity (potent insecticidal activity on agricultural and sanitary harmful insects, as well as action that activates nerves).

The nitroimino-imidazolidine compounds A1 and A2 can be prepared comparatively easily in a solvent in which a base is present.

The nitroimino-imidazolidine compounds A1 and A2 each can have halogen atoms. Consequently, an insecticide that contains as its active ingredient the nitroimino-imidazolidine compound A1 or A2 having halogen atoms has superior insecticidal effects against agricultural and sanitary harmful insects.

Examples of the present invention and Comparative examples will be described below.

EXAMPLE 1

Preparation of 1,3-bis[(6-chloronicotinyl)-2-nitroiminoimidazolidin-3-yl]propane Sodium hydride (60% oil dispersion, 0.17 g, 4.25 mmol) was suspended in 10 ml of DMF. 1-(6-Chloronicotinyl)-2-nitroiminoimidazolidine (1.03 g, 4 mmol), which is commonly referred to as imidacloprid), was added to this suspension. This mixture was then stirred for 1 hour at room temperature. A solution of 1,3-diiodopropane (0.58 g, 2 mmol) in DMF (10 ml) was then added dropwise to this reaction mixture over the course of 30 minutes while cooling with ice. Following completion of dropping, the reaction mixture was stirred at room temperature for 4 hours.

The DMF was distilled off under reduced pressure from the reaction mixture. The residue was added to a mixture of water and chloroform and the resulting mixture was shaken. After separating the chloroform layer and drying, the solvent was distilled off under reduced pressure. The semi-solid residue was then subjected to silica gel column chromatography with a 15:1 (v/v) mixture of ethyl acetate and ethanol as the eluate. The crude product was recrystallized from methanol. The yield of crystalline product was 0.95 g (77%), and the melting point was 139 to 141° C. These crystals were then subjected to elementary analysis and NMR (nuclear magnetic resonance) analysis. Those results are shown below.

Elementary Anal., Found (Calc.): C, 45.80; (45.74), H, 4.50; (4.39), N, 25.50; (25.40).

NMR (CDCl$_3$, δ, ppm):2.00 (2H, quint, J=7.0), 3.36 (4H, t, J=7.0), 3.66 (4H, m), 3.80 (4H, m), 4.50 (4H, s), 7.37 (2H, d, J=8.0), 7.54 (2H, dd, J=8.0/2.6), 8.34 (2H, d, J=2.6).

Based on the results of analysis, the compound of Example 1 was determined to be 1,3-bis[(6-chloronicotinyl)-2-nitroiminoimidazolidin-3-yl]propane having the structural formula indicated below.

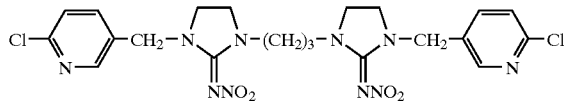

EXAMPLE 2

Preparation of 1,4-bis[(6-chloronicotinyl)-2-nitroiminoimidazolidin-3-yl]butane

The procedure of Example 1 was carried out analogously except that 1,4-diiodobutane was used instead of the 1,3-diiodopropane used in Example 1. The melting point of the crystalline product was 186 to 188° C. The results of elementary analysis and NMR analysis are shown below.

Elementary Anal., Found (Calc.): C, 46.80; (46.73), H, 4.60; (4.64), N, 24.90; (24.77).

$^1$H-NMR (CDCl$_3$, δ, ppm; J Hz): 1.51 (4H, bs) , 3.21 (4H, bs), 3.66 (4H, m), 3.73 (4H, m), 4.44 (4H, s), 7.54 (2H, d, J=7.7), 7.78 (2H, dd, J=7.7/2.8), 8.35 (2H, d, J=2.8).

Based on the results of analysis, the compound of Example 2 was determined to be 1,4-bis[(6-chloronicotinyl)-2-nitroiminoimidazolidin-3-yl]butane having the structural formula indicated below.

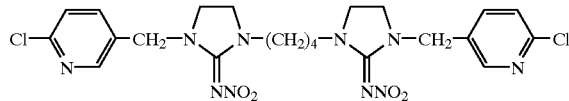

EXAMPLE 3

Preparation of 1,5-bis[(6-chloronicotinyl)-2-nitroiminoimidazolidin-3-yl]pentane The procedure of Example 1 was carried out analogously except that 1,5-diiodopentane was used instead of the 1,3-diiodopropane of Example 1. The melting point of the crystalline product was 140 to 142° C. The results of elementary analysis and NMR analysis are shown below.

Elementary Anal., Found (Calc.): C, 47.80; (47.67), H,4.68 (4.87), N,24.00; (24.17).

$^1$H-NMR (CDCl$_3$, δ, ppm): 1.36 (2H, m), 1.66 (4H, m), 3.35 (4H, t, J=7.0), 3.66 (4H, m), 3.80 (4H, m), 4.48 (4H, s), 7.36 (2H, d, J=8.6), 7.71 (2H, dd, J=8.6/1.8), 8.34 (2H, d, J=1.8).

Based on the results of analysis, the compound of Example 3 was determined to be 1,5-bis[(6-chloronicotinyl)-2-nitroiminoimidazolidin-3-yl]pentane having the structural formula indicated below.

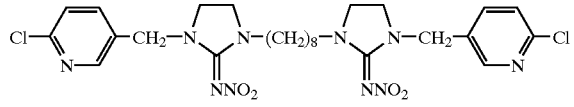

EXAMPLE 4

Preparation of 1,6-bis[(6-chloronicotinyl)-2-nitroiminoimidazolidin-3-yl]hexane

The procedure of Example 1 was carried out analogously except that 1,6-diiodohexane was used instead of the 1,3-diiodopropane of Example 1. The melting point of the crystalline product was 139 to 141° C. The results of elementary analysis and NMR analysis are shown below.

Elementary Anal., Found (Calc.): C, 48.80; (48.57), H, 4.98; (5.10), N, 24.00; (23.60).

$^1$H-NMR (CDCl$_3$, δ, ppm): 1.34 (4H, m), 1.62 (4H, m), 3.33 (4H, t, J=7.0), 3.63 (4H, m), 3.77 (4H, m), 4.47 (4H, s), 7.35 (2H, d, J=8.0), 7.72 (2H, dd, J=8.0/1.8), 8.33 (2H, d, J=1.8).

Based on the results of analysis, the compound of Example 4 was determined to be 1,6-bis[(6-chloronicotinyl)-2-nitroiminoimidazolidin-3-yl]hexane having the structural formula indicated below.

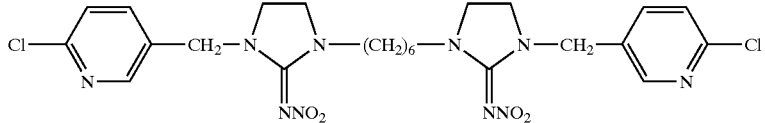

EXAMPLE 5

Preparation of 1,7-bis[(6-chloronicotinyl)-2-nitroiminoimidazolidin-3-yl]heptane The procedure of Example 1 was carried out analogously except that 1,7-diiodoheptane was used instead of the 1,3-diiodopropane of Example 1. The product thus obtained was in the form of liquid. The results of elementary analysis and NMR analysis are shown below.

Elementary Anal., Found (Calc.): C, 49.30; (49.42), H, 5.08; (5.31), N, 23.00; (23.06).

$^1$H-NMR (CDCl$_3$, δ, ppm): 1.32 (6H, m), 1.61 (4H, m), 3.32 (4H, t, J=7.0), 3.66 (4H, m), 3.79 (4H, m), 4.47 (4H, s), 7.35 (2H, d, J=8.4), 7.71 (2H, dd, J=8.4/2.6), 8.33 (2H, d, J=2.6).

Based on the results of analysis, the compound of Example 5 was determined to be 1,7-bis[(6-chloronicotinyl)-2-nitroiminoimidazolidin-3-yl]heptane having the structural formula indicated below.

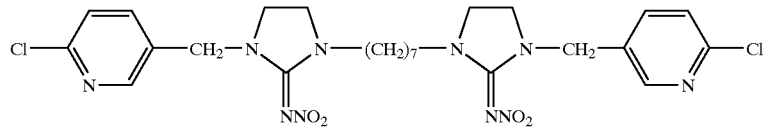

EXAMPLE 6

Preparation of 1,8-bis[(6-chloronicotinyl)-2-nitroiminoimidazolidin-3-yl]octane

The procedure of Example 1 was carried out analogously except that 1,8-diiodooctane was used instead of the 1,3-diiodopropane of Example 1. The product thus obtained was in the form of liquid. The results of elementary analysis and NMR analysis are shown below.

Elementary Anal., Found (Calc.): C, 50.30; (50.24), H, 5.48; (5.51), N, 23.00; (22.54).

$^1$H-NMR (CDCl$_3$, δ, ppm): 1.30 (8H, m), 1.60 (4H, m), 3.26 (4H, t, J=7.0), 3.60 (4H, m), 3.76 (4H, m), 4.47 (4H, s), 7.36 (2H, d, J=8.4), 7.72 (2H, dd, J=8.4/2.6), 8.32 (2H, d, J=2.6).

Based on the results of analysis, the compound of Example 6 was determined to be 1,8-bis[(6-chloronicotinyl)-2-nitroiminoimidazolidin-3-yl]octane having the structural formula indicated below.

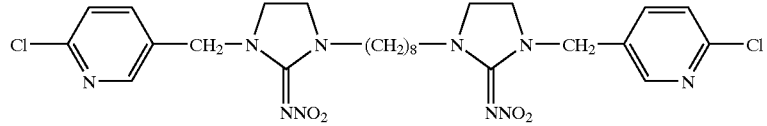

EXAMPLE 7

Preparation of 1,9-bis[(6-chloronicotinyl)-2-nitroiminoimidazolidin-3-yl]nonane

The procedure of Example 1 was carried out analogously except that 1,9-diiodononane was used instead of the 1,3-diiodopropane of Example 1. The product thus obtained was in the form of liquid. The results of elementary analysis and NMR analysis are shown below.

Elementary Anal., Found (Calc.): C, 50.30; (51.02), H, 5.48; (5.71), N, 23.00; (22.04).

$^1$H-NMR (CDCl$_3$, δ, ppm): 1.33 (6H, m), 1.60(8H, m), 3.33 (4H, t, J=13.2), 3.62 (4H, m), 3.78 (4H, m), 4.47 (4H, s), 7.35 (2H, d, J=8.2), 7.70 (2H, dd, J=8.2/2.2), 8.27 (2H, d, J=2.2).

Based on the results of analysis, the compound of Example 7 was determined to be 1,9-bis[(6-chloronicotinyl)-2-nitroiminoimidazolidin-3-yl]nonane having the structural formula indicated below.

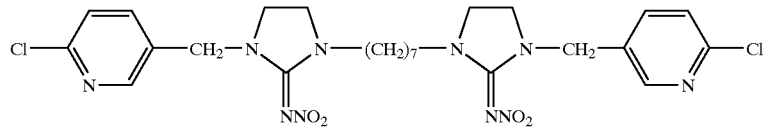

EXAMPLE 8

Preparation of 1,10-bis[(6-chloronicotinyl)-2-nitroiminoimidazolidin-3-yl]decane The procedure of Example 1 was carried out analogously except that 1,10-diiododecane was used instead of the 1,3-diiodopropane of Example 1. The melting point of the crystalline product was 77 to 79° C. The results of elementary analysis and NMR analysis are shown below.

Elementary Anal., Found (Calc.): C, 51.40; (51.77), H, 5.68; (5.90), N, 22.00; (21.56).

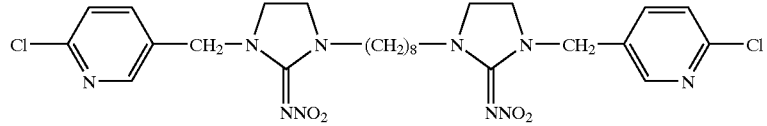

$^1$H-NMR (CDCl$_3$, δ, ppm): 1.28 (12H, m), 1.60 (4H, m), 3.30 (4H, t, J=7.0), 3.60 (4H, m), 3.75 (4H, m), 4.47 (4H, s), 7.35 (2H, d, J=8.1), 7.72 (2H, dd, J=8.1/2.2), 8.32 (2H, d, J=2.2).

Based on the results of analysis, the compound of Example 8 was determined to be 1,10-bis[(6-chloronicotinyl)-2-nitroiminoimidazolidin-3-yl]decane having the structural formula indicated below.

EXAMPLE 9

Preparation of 1,4-bis[(6-chloronicotinyl)-2-nitroiminoimidazolidin-3-yl]-2-butene Imidacloprid (3.37 g, 12 mmol), 1,4-dibromo-2-butene (1.60 g, 6 mmol), and potassium carbonate (1.83 g, 12 mmol) were mixed in 30 ml of acetonitrile, and the mixture was refluxed for 19 hours. After distilling off the solvent under reduced pressure, the residue was extracted with chloroform, and the chloroform layer was dried over magnesium sulfate. After distilling off the solvent, the residue was then subjected to silica gel column chromatography with a mixed solvent of ethyl acetate and ethanol (15:1 (v/v)) as the eluate. The crude product was purified by recrystallizing from ethanol. The yield of crystalline product was 0.22 g (7%), and the melting point was 199 to 202° C. The results of elementary analysis and NMR analysis are shown below.

Elementary Anal., Found (Calc.): C, 49.80; (46.90), H, 4.40; (4.29), N, 25.01; (24.86).

NMR (DMSO-d$_6$, δ, ppm): 3.83 (4H, d, J=3.6), 5.71 (2H, t, J=3.6), 3.62–3.75 (4H, m), 4.75 (4H, s), 7.50 (2H, d, J=8.4), 7.78 (2H, dd, J=8.4/2.2), 8.36 (2H, d, J=2.2).

Based on the results of analysis, the compound of Example 9 was determined to be 1,4-bis[(6-chloronicotinyl)-2-nitroiminoimidazolidin-3-yl]-2-butene having the structural formula indicated below.

EXAMPLE 10

Preparation of 1,4-bis[(6-chloronicotinyl)-2-nitroiminoimidazolidin-3-yl]-2-butyne The procedure of Example 9 was carried out analogously except that 1,4-dibromo-2-butyne was used instead of the 1,4-dibromo-butene of Example 9. The melting point of the crystalline product was 207 to 209° C. The results of elementary analysis and NMR analysis are shown below.

Elementary Anal., Found (Calc.): C, 46.80; (47.07), H, 4.02; (3.95), N, 25.21; (24.95).

NMR (DMSO-d$_6$, δ, ppm): 1.28 (12H, m), 1.60 (4H, m), 3.30 (4H, t, J=7.0), 3.60 (4H, m), 3.75 (4H, m), 4.47 (4H, s), 7.35 (2H, d, J=8.1), 7.72 (2H, dd, J=8.1/2.2), 8.32 (2H, d, J=2.2).

Based on the results of analysis, the compound of Example 10 was determined to be 1,4-bis[(6-chloronicotinyl)-2-nitroiminoimidazolidin-3-yl]-2-butyne having the structural formula indicated below.

EXAMPLE 11

Preparation of bis 3-[(6-chloronicotinyl)-2-nitroiminoimidazolidin-3-yl]propyl ether The procedure of Example 1 was carried out analogously except that bisparatoluenesulfonic acid 4-oxa 1,7-heptadiyl was used instead of the 1,3-diiodopropane of Example 1. The melting point of the crystalline product was 128 to 131° C. The results of elementary analysis and NMR analysis are shown below.

Elementary Anal., Found (Calc.): C, 46.99; (47.29), H, 5.02; (4.96), N, 23.21; (23.00).

NMR (CDCl$_3$, δ, ppm): 3.83 (4H, d, J=3.6), 3.62–3.75 (4H, m), 4.75 (4H, s), 5.71 (2H, t, J=3.6), 7.50 (2H, d, J=8.4), 7.78 (2H, dd, J=8.4/2.2), 8.36 (2H, d, J=2.2).

Based on the results of analysis, the compound of Example 11 was determined to be bis 2-[(6-chloronicotinyl)-2-nitroiminoimidazolidin-3-yl]propyl ether having the structural formula indicated below.

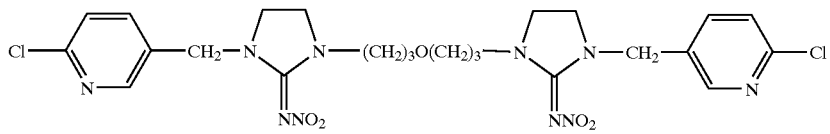

EXAMPLE 12

Preparation of 1,3-bis[(6-chloronicotinyl)-2-nitroiminoimidazolidin-3-yl]methylbenzene The procedure of Example 1 was carried out analogously except that 1,3-bischloromethylbenzene was used instead of the 1,3-diiodopropane of Example 1. The melting point of the crystalline product was 150 to 153° C. The results of elementary analysis and NMR analysis are shown below.

Elementary Anal., Found (Calc.): C, 50.99; (50.90), H, 4.02; (4.27), N, 22.21; (22.83).

NMR (acetone-$d_6$, δ, ppm): 4.45 (4H, s), 3.60–3.70 (4H, m), 4.48 (4H, s), 7.23 ($^1$H, t, J=1.1), 7.28 (2H, dd, J=7.7/1.1), 7.41($^1$H, t, J=7.7), 7.55 (2H, d, J=8.0), 7.82 (2H, dd, J=8.0/2.5), 8.38 (2H, d, J=2.5).

Based on the results of analysis, the compound of Example 12 was determined to be 1,3-bis[(6-chloronicotinyl)-2-nitroiminoimidazolidin-3-yl]methylbenzene having the structural formula indicated below.

EXAMPLE 13

Preparation of 1,4-bis[(6-chloronicotinyl)-2-nitroiminoimidazolidin-3-yl]methylbenzene The procedure of Example 1 was carried out analogously except that 1,4-bischloromethylbenzene was used instead of the 1,3-diiodopropane of Example 1. The melting point of the crystalline product was 204 to 206° C. The results of elementary analysis and NMR analysis are shown below.

Elementary Anal., Found (Calc.): C, 50.89; (50.90), H, 4.12; (4.27), N, 22.61; (22.83).

NMR (acetone-$d_6$, δ, ppm): 4.51 (4H, s), 3.70–3.77 (4H, m), 4.55 (4H, s), 7.38 (4H, s), 7.46 (2H, d, J=8.0), 7.86 (2H, dd, J=8.0/2.6), 8.41 (2H, d, J=2.6).

Based on the results of analysis, the compound of Example 13 was determined to be 1,4-bis[(6-chloronicotinyl)-2-nitroiminoimidazolidin-3-yl]methylbenzene having the structural formula indicated below.

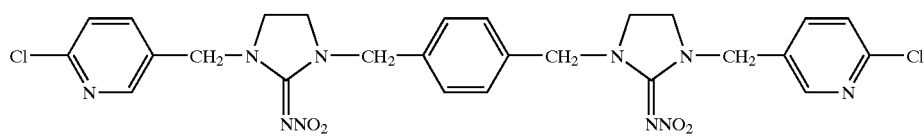

EXAMPLE 14

Preparation of 1,6-bis[1-(2-chloro-5-thiazolylmethyl)-2-nitroiminoimidazolidin-3-yl] hexane A suspension of sodium hydride (60%, 0.48 g, 12 mmol) in 20 ml of DMF was prepared. 1-(2-Chloro-5-thiazolylmethyl)-2-nitroiminoimidazolidine (2.61 g, 10 mmol) was added to this suspension. The resulting mixture was then stirred for 1 hour at room temperature. 1,6-Diiodohexane (1.64 g, 5 mmol) was added dropwise to this reaction mixture over the course of 30 minutes while cooling the reaction mixture with ice. Following completion of dropping, the mixture was stirred for 4 hours at room temperature. The DMF was distilled off from the reaction mixture under reduced pressure. The residue was then shaken with a mixture of water and chloroform. After separating the chloroform layer and drying, the solvent was distilled off under reduced pressure. The semi-solid residue was subjected to silica gel column chromatography with a mixture (15:1 (v/v)) of ethyl acetate and ethanol as the eluate. The crude product was recrystallized from methanol. The yield of crystalline product was 0.22 g (70%), and the melting point was 204 to 206° C. The results of elementary analysis and NMR analysis are shown below.

Elementary Anal., Found (Calc.): C, 36.80; (36.67), H, 4.51; (4.33), N, 23.50; (23.13).

NMR (CDCl$_3$, δ, ppm): 1.34 (4H, m), 1.60 (4H, m), 3.32 (4H, t, J=7.3), 3.66 (4H, m), 3.77 (4H, m), 4.57 (4H, s), 7.49 (2H, s).

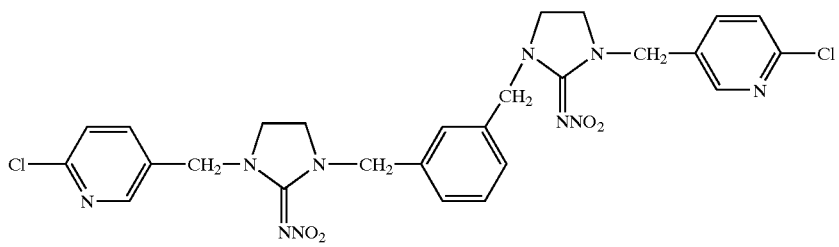

Based on the results of analysis, the compound of Example 14 was determined to be 1,6-bis[1-(2-chloro-5-thiazolylmethyl)-2-nitroiminoimidazolidin-3-yl]hexane having the structural formula indicated below.

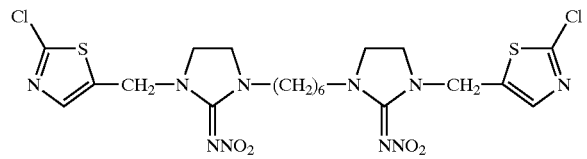

COMPARATIVE EXAMPLE 1

Preparation of 1,2-bis[[(6-chloronicotinyl)-2-nitroiminoimidazolidin-3-yl]ethane 1-(6-Chloronicotinyl)-2-nitroiminoimidazolidine (128 mg, 0.5 mmol), ethane 1,2-bistosylate (92 mg, 0.25 mmol), and potassium carbonate (160 mg, 1.16 mmol) were suspended in a mixture of THF (4.5 ml) and DMF (0.5 ml). This suspension was heated for 50 hours at the boiling point of THF. The residue obtained by distilling off the THF under reduced pressure was subjected to silica gel column chromatography with a mixture (15:1 (v/v)) of ethyl acetate and ethanol as the eluate. The crude product was recrystallized from ethanol. The yield of crystalline product was 0.22 g (7%), and the melting point was 197 to 198° C. These crystals were then subjected to elementary analysis and NMR analysis. Those results are shown below.

Elementary Anal., Found (Calc.): C, 45.00; (44.70), H, 4.10; (4.13), N, 26.30; (26.07).

NMR (DMSO-$d_6$, δ, ppm): 3.50 (4H, s), 3.67 (2H, m), 3.78 (2H, m), 4.40 (4H, s), 7.48 (2H, d, J=8.0), 8.20 (2H, dd, J=8.0/2.5), 8.38 (2H, d, J=2.5).

Based on the results of analysis, the compound of Comparative Example 1 was determined to be 1,2-bis[(6-chloronicotinyl)-2-nitroiminoimidazolidin-3-yl]ethane having the structural formula indicated below.

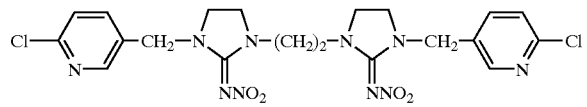

The insecticidal activity against the common cockroach was tested for the compounds of Examples 1 to 14 and the compound of Comparative Example 1. Methanol solutions containing 1% by weight of each compound were prepared. 1 to 10 μl of the methanol solution were injected into the abdomens of 3 male adult common cockroaches. The concentration at which two of the three adult insects became paralyzed or died, namely the minimum lethal dose (MLD: moles/insect) was then investigated. The values of log(1/MLD) are shown in Table 1.

TABLE 1

| Compound | log (1/MLD) |
|---|---|
| Exp. 1 | 8.31 |
| Exp. 2 | 7.97 |
| Exp. 3 | 8.41 |
| Exp. 4 | 8.65 |
| Exp. 5 | 8.55 |

TABLE 1-continued

| Compound | log (1/MLD) |
|---|---|
| Exp. 6 | 8.35 |
| Exp. 7 | 8.56 |
| Exp. 8 | 8.43 |
| Exp. 9 | 8.43 |
| Exp. 10 | 7.52 |
| Exp. 11 | 8.23 |
| Exp. 12 | 7.71 |
| Exp. 13 | 7.57 |
| Exp. 14 | 7.56 |
| Comp. Exp. 1 | 7.38 |

The compounds of Examples 1 to 14 demonstrated larger values for log(1/MLD) as compared with the compound of Comparative Example 1, and the insecticidal performance of these compounds was higher. The insecticidal effects of Examples 1 to 9 and Example 11 were particularly high. It should be noted that the values are shown in the form of logarithmic values.

It should be apparent to those skilled in the art that the present invention may be embodied in many other specific forms without departing from the spirit or scope of the invention. For example, the present invention may be modified in the manner described below.

By-products such as hydrogen halide (HD) may be forcibly removed from the reaction system in the preparation process of nitroimino-imidazolidine compound A1 or A2. In this case, the reaction rate improves, and the yield of the desired product increases.

A dihydroxy compound or dialkoxy compound can be used instead of the dihalogen compound of chemical formula 6. The nitroimino-imidazolidine compound A1 or A2 can be prepared by a dehydration reaction between imidazolidine and dihydroxy compound or by a dealcoholation reaction between imidazolidine and dialkoxy compound.

The insecticide against sanitary harmful insects may also be used as a pesticide that eradicates, for example, fleas and lice found on animals other than humans such as dogs and cats.

The insecticide for agricultural or sanitary harmful insects may also be used for controlling harmful insects that proliferate during storage or harmful insects found in building interiors.

The present examples and embodiments are not restrictive and the invention is not to be limited to the details given herein, but may be modified within the scope and equivalence of the appended claims.

What is claimed is:

1. A compound represented by chemical formula 1:

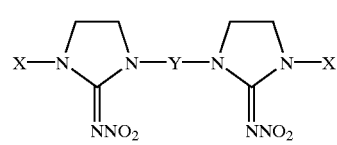

(1)

wherein Y represents an alkylene group having 3 to 10 carbon atoms, —$CH_2CH$=$CHCH_2$—, —$CH_2C$≡$CCH_2$—, —$(CH_2)_3O(CH_2)_3$—, —$(CH_2)_3S(CH_2)_3$—,

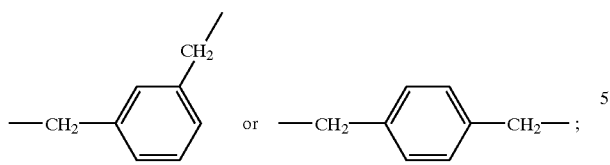

X represents a pyridylmethyl group composed of

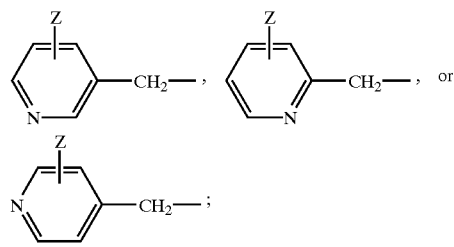

and Z represents a halogen atom, $CH_3$ or H.

2. A process for preparing a compound represented by chemical formula 1:

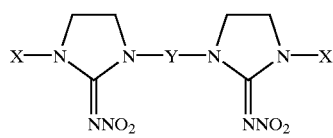 (1)

where in Y represents an alkylene group having 3 to 10 carbon atoms, $-CH_2CH=CHCH_2-$, $-CH_2C\equiv CCH_2-$, $-(CH_2)_3O(CH_2)_3-$, $-(CH_2)_3S(CH_2)_3-$,

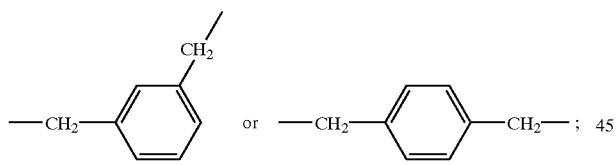

X represents a pyridylmethyl group composed of

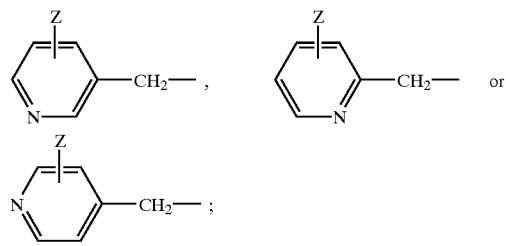

and Z represents a halogen atom, $CH_3$, or H, the process comprising a step of reacting 1-(pyridylmethyl)-2-nitroiminoimidazolidine represented by chemical formula 3 with a compound represented by chemical formula 4 in the presence of a base and in a solvent:

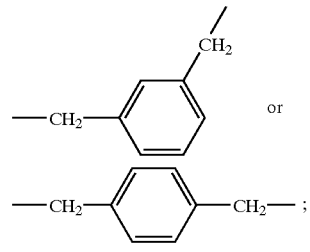 (3)

wherein X represents a pyridylmethyl group composed of

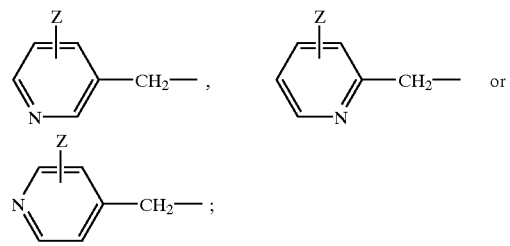

and Z represents a halogen atom, $CH_3$, or H, and $$D-Y-D \quad (4),$$

wherein Y represents an alkylene group having 3 to 10 carbon atoms, $-CH_2CH=CHCH_2-$, $-CH_2C\equiv CCH_2-$, $-(CH_2)_3O(CH_2)_3-$, $-(CH_2)_3S(CH_2)_3-$,

and D represents Cl, Br, I, or

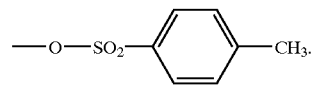

3. The process according to claim 2, wherein the molar ratio of the compound represented by chemical formula 4 to the compound represented by chemical formula 3 is from 0.5:1 to 1.2:1.

4. The process according to claim 2, wherein the molar ratio of the base to the compound represented by chemical formula 3 is from 0.5:1 to 2.0:1.

5. The process according to claim 2, wherein the reaction step is carried out at 0 to 200° C.

6. The process according to claim 2, wherein the reaction step is carried out under the atmospheric pressure.

7. The process according to claim 2, wherein the reaction step is carried out for 30 minutes to 24 hours.

8. An insecticide composition comprising a compound having the chemical formula:

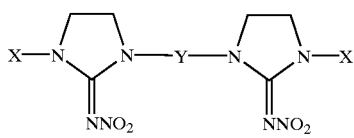
(1)

wherein Y represents an alkylene group having 3 to 10 carbon atoms, —CH$_2$CH=CHCH$_2$—, —CH$_2$C≡CCH$_2$—, —(CH$_2$)$_3$O(CH$_2$)$_3$—, —(CH$_2$)$_3$S(CH$_2$)$_3$—,

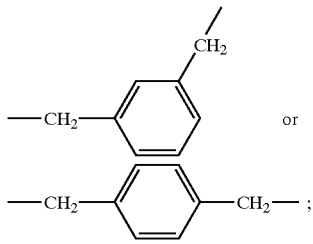 or

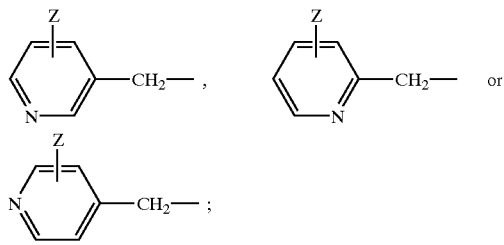 ;

X represents a pyridylmethyl group composed of

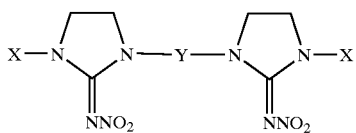

and Z represents a halogen atom, CH$_3$, or H.

9. A method for killing insects, said method comprising the step of administering to the insects a lethal amount of a composition that comprises at least one compound having the general formula:

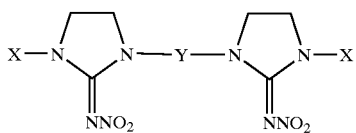
(1)

wherein Y represents an alkylene group having 3 to 10 carbon atoms, —CH$_2$CH=CHCH$_2$—, —CH$_2$C≡CCH$_2$—, —(CH$_2$)$_3$O(CH$_2$)$_3$—, —(CH$_2$)$_3$S(CH$_2$)$_3$—,

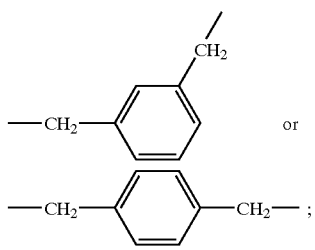 or

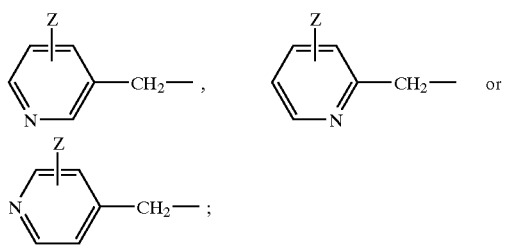 ;

X represents a pyridylmethyl group composed of

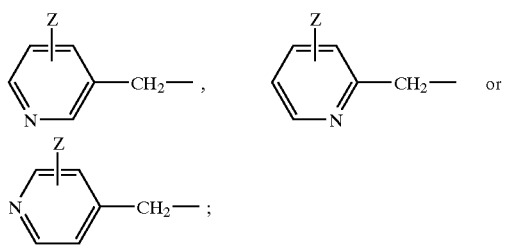

and Z represents a halogen atom, CH$_3$, or H.

* * * * *